United States Patent
Dehestani

(10) Patent No.: US 11,478,521 B2
(45) Date of Patent: Oct. 25, 2022

(54) METHODS FOR PREPARATION OF CANNABIS OIL EXTRACTS AND COMPOSITIONS

(71) Applicant: Cannacraft, Inc., Santa Rosa, CA (US)

(72) Inventor: Ahmad Dehestani, Walnut Creek, CA (US)

(73) Assignee: Cannacraft, Inc., Santa Rosa, CA (US)

( * ) Notice: Subject to any disclaimer, the term of this patent is extended or adjusted under 35 U.S.C. 154(b) by 127 days.

(21) Appl. No.: 17/150,408

(22) Filed: Jan. 15, 2021

(65) Prior Publication Data

US 2021/0236573 A1     Aug. 5, 2021

Related U.S. Application Data

(60) Provisional application No. 62/962,557, filed on Jan. 17, 2020.

(51) Int. Cl.
*A61K 36/00*     (2006.01)
*A61K 36/185*     (2006.01)

(52) U.S. Cl.
CPC ...... *A61K 36/185* (2013.01); *A61K 2236/331* (2013.01); *A61K 2236/35* (2013.01); *A61K 2236/55* (2013.01)

(58) Field of Classification Search
None
See application file for complete search history.

(56) References Cited

FOREIGN PATENT DOCUMENTS

JP     2006516235     *   6/2006

* cited by examiner

*Primary Examiner* — Michael V Meller
(74) *Attorney, Agent, or Firm* — Fox Rothschild LLP

(57) ABSTRACT

Systems and methods for removing sulfur from a *cannabis* product are provided. The method includes dissolving, in a solvent, the *cannabis* product including sulfur, forming a dissolved solution, and mixing an oxidation agent into the dissolved solution, causing the dissolved solution to form into a plurality of solutions. The plurality of solutions include a water solution and an organic solution, the water solution includes sulfur, and the organic solution includes the *cannabis* product. The method further includes removing the water solution from the plurality of solutions.

2 Claims, 1 Drawing Sheet

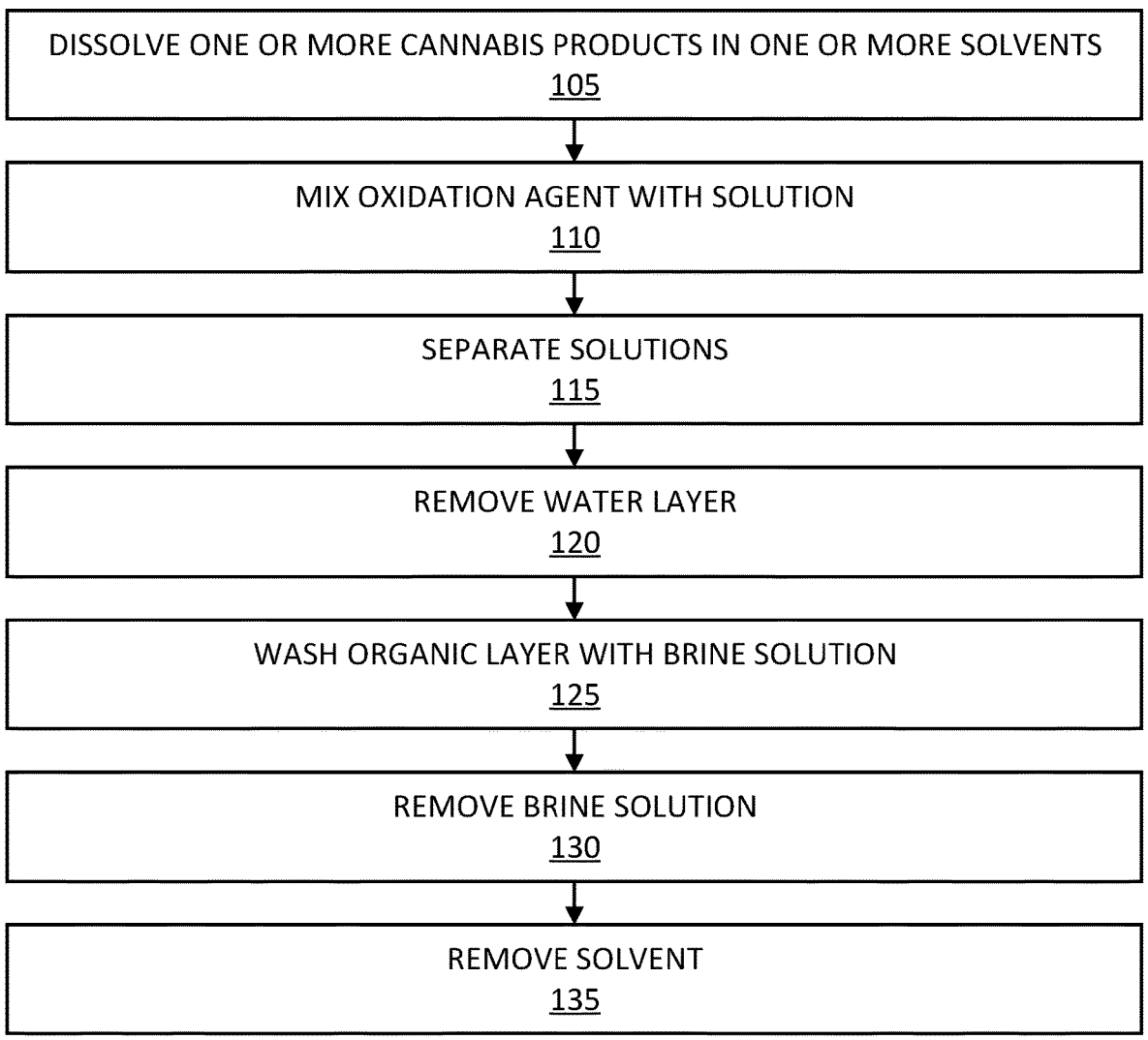

METHODS FOR PREPARATION OF CANNABIS OIL EXTRACTS AND COMPOSITIONS

CROSS-REFERENCE TO RELATED APPLICATIONS

This application claims priority under 35 U.S.C. § 119(e) to U.S. Provisional Application No. 62/962,557, filed Jan. 17, 2020, the disclosure of which is incorporated herein by reference in its entirety.

FIELD OF THE INVENTION

The present disclosure relates to *cannabis* oil preparation and, in particular, to methods for removing sulfur from *cannabis* products, such as natural cannabinoids, cannabinoid aetates, and cannabinoid carboxylates, during the preparation of *cannabis* oil.

BACKGROUND

*Cannabis* products originate with commercially grown *cannabis* crops. As with many commercially grown crops, fertilizers are used in the production of *cannabis*. Fertilizing crops is an essential step in the cultivation of a healthy and bountiful crop. Due to their importance, there are a large variety of fertilizers on the market containing a variety of chemicals, such as sulfur. As a result, many *cannabis* products have come into contact with sulfur.

Sulfur is an elemental chemical that has been used in the farming industry as a component of a variety of fertilizers and is registered in the United States by the Environmental Protection Agency ("EPA") for use as an insecticide, fungicide, and rodenticide on several hundred food and feed crops on ornamental, turf, and residential sites. It is considered green for insecticides and fungicides.

Sulfur poses a challenge in the *cannabis* industry. During the extraction process, sulfur is taken up and made into distillate. This results in a sulfur smell being generated during the extraction process and result in a sour taste to the distillate. Therefore, it is essential to remove the sulfur from *cannabis* products prior to distributing *cannabis* products in the marketplace.

For at least these reasons, a versatile and cost-effective means of removing sulfur from *cannabis* products is needed.

SUMMARY

According to an aspect of the present disclosure, a method for removing sulfur from a *cannabis* product is provided. The method includes dissolving, in a solvent, the *cannabis* product including sulfur, forming a dissolved solution, and mixing an oxidation agent into the dissolved solution, causing the dissolved solution to form into a plurality of solutions. The plurality of solutions include a water solution and an organic solution, the water solution includes sulfur, and the organic solution includes the *cannabis* product. The method further includes removing the water solution from the plurality of solutions.

According to various embodiments, the method further includes washing the organic solution with a brine solution, and removing the brine solution.

According to various embodiments, the method further includes removing the solvent from the organic solution in a reduced pressure.

According to various embodiments, the *cannabis* product is a distilled *cannabis* material.

According to various embodiments, the *cannabis* product is a crude *cannabis* material.

According to various embodiments, the solvent is a non-water soluble miscible solvent.

According to various embodiments, the solvent is an organic solvent.

According to various embodiments, the non-water soluble miscible solvent is an organic solvent.

According to various embodiments, the oxidation agent includes sodium perchlorate.

According to various embodiments, the non-water soluble miscible solvent includes at least one solvent selected from the group consisting of: an alkane; and an aromatic.

According to another aspect of the present disclosure, a method for removing sulfur from a *cannabis* product is provided. The method includes dissolving the *cannabis* product in a non-water soluble miscible solvent, forming a dis-solved solution, and mixing an oxidation agent into the dissolved solution, causing the dissolved solution to form into a plurality of solutions. The plurality of solutions include a water solution and an organic solution, the water solution includes sulfur, and the organic solution includes the *cannabis* product. The method further includes removing the water solution from the plurality of solutions, washing the organic solution with a brine solution, and removing the brine solution.

According to various embodiments, the non-water soluble miscible solvent is an organic solvent.

According to various embodiments, the oxidation agent includes sodium perchlorate.

According to various embodiments, the non-water soluble miscible solvent includes at least one solvent selected from the group consisting of: an alkane; and an aromatic.

According to various embodiments, the *cannabis* product is a distilled *cannabis* material.

According to various embodiments, the *cannabis* product is a crude *cannabis* material.

BRIEF DESCRIPTION OF THE DRAWINGS

FIG. 1 illustrates a flowchart of a method for removing sulfur from a *cannabis* product, in accordance with various embodiments of the present disclosure.

DETAILED DESCRIPTION

Some implementations of the present disclosure will now be described more fully hereinafter. Indeed, various implementations of the disclosure may be embodied in many different forms and should not be construed as limited to the implementations set forth herein; rather, these example implementations are provided so that this disclosure will be thorough and complete, and will fully convey the scope of the disclosure to those skilled in the art.

As used in this document, the singular forms "a," "an," and "the" include plural references unless the context clearly dictates otherwise. Unless defined otherwise, all technical and scientific terms used herein have the same meanings as commonly understood by one of ordinary skill in the art. As used in this document, the term "comprising" (or "comprises") means "including (or includes), but not limited to." When used in this document, the term "exemplary" is intended to mean "by way of example" and is not intended to indicate that a particular exemplary item is preferred or required.

Systems and methods for removing sulfur from a *cannabis* product (e.g., *cannabis* oil) are provided. The disclosed systems and methods of the present disclosure are suitable for removing sulfur from various *cannabis* products containing, for example, natural cannabinoids, cannabinoid acetates, cannabinoid carboxylates, or the like.

A. Methods for Removing Sulfur from *Cannabis* Products

As shown in FIG. 1, a method 100 for removing sulfur from a *cannabis* product is illustratively depicted, in accordance with various embodiments of the present disclosure.

The methods of the present disclosure include, at 105, dissolving one or more *cannabis* products into a non-water miscible solvent, usually an organic solvent. The solvents are configured to dissolve the one or more *cannabis* products and the sulfur.

According to various embodiments, the *cannabis* product includes a crude and/or distillate *cannabis* material. The crude *cannabis* material may include one or more water soluble sulfur oxides. The distillate *cannabis* material may have low solubility in organic solvents such as, but not limited to, pentane. According to various embodiments, the solvent has a high solubility of sulfur at a particular temperature range. The temperature range may be from approximately 0 to 100 degrees Celsius. For example, this temperature can be about 10 degrees C., about 20 degrees C., about 30 degrees C., about 40 degrees C., about 45 degrees C., about 50 degrees C., about 55 degrees C., about 60 degrees C., about 65 degrees C., about 70 degrees C., about 75 degrees C., about 80 degrees C., or in the range of 60-80 degrees C., 65-75 degrees C., 55-85 degrees C., and the like.

According to various embodiments, various solvents and/or oxidants may be used during the process of extracting the sulfur. According to various embodiments, non-water-miscible solvents such as, but not limited to, alkanes and aromatics (e.g., benzene, toluene, etc.) may be used. The solvent or solvents may include hydrocarbons, aromatics, halogenated organic solvents, amines, acetates, and/or any other suitable solvents.

The *cannabis* products may include, but are not limited to, cannabidiol ("CBD"), cannabidiolic acid ("CBDA"), tetrahydrocannabinolic acid ("THCA"), cannabinolic acid ("CBNA"), cannabigerolic acid ("CBGA"), tetrahydrocannabinolic acid ("THCA"), and/or all other carboxylate *cannabis* material and/or their acetate as well as both of their forms.

Following the dissolution of the one or more *cannabis* products and the sulfur, the solution, at 110, is mixed with an oxidation agent. The oxidation agent may include sodium perchlorate. It is noted, however, that other oxidation agents may be used, while maintaining the spirit of the present disclosure. The oxidants used are able to oxidize elemental sulfur from any corresponding water soluble sulfur oxides.

The solutions, at 115, are then allowed to separate into two solutions, including a lower water layer. At 120, the lower water layer is removed, which contains the water-soluble material, leaving the remaining solution, an organic *cannabis* layer which contains the *cannabis* product. If needed, more washing of the *cannabis* layer may be performed to remove more of the sulfur. According to various embodiments, the *cannabis* layer (e.g., an organic *cannabis* layer), at 125, is washed at least one more time with a brine solution. The solutions (*cannabis* layer and brine solution) are then allowed to separate into two solutions, and the brine solution, at 130, is then removed, leaving the *cannabis* layer.

Once the *cannabis* layer, including the solvent, is isolated, the solvent, at 135, is removed under reduced pressure to produce a substantially sulfur free crude or distillate *cannabis* material.

According to various embodiments, the above-illustrated example may be performed wherein the *cannabis* product is THCA, CBDA, CBGA, and/or all carboxylate *cannabis* material.

The solvent system can be formed of one or more solvents that are added to the *cannabis* products in a step-wise fashion. In one example, the solvent system comprises a first solvent and a second solvent. In some embodiments, the method includes contacting the *cannabis* product with the first solvent, followed by adding and mixing the second solvent.

In some embodiments, the method for removing sulfur from a *cannabis* product comprises: (a) mixing a first solvent with a *cannabis* product; (b) mixing the resulting solution with a second solvent, thereby causing the sulfur to partition into a solvent layer containing the second solvent; and (c) removing the solvent layer containing the second solvent so that the resulting *cannabis* product contains a reduced amount of sulfur.

While certain embodiments of the invention have been described using specific terms, such description is for present illustrative purposes only, and it is to be understood that changes and variations to such embodiments, including but not limited to the substitution of equivalent features or parts, and the reversal of various features thereof, may be practiced by those of ordinary skill in the art without departing from the spirit or scope of the present disclosure.

An illustrative example is herein described:

According to the illustrative example, a five-liter conical glass reactor is presented with a mechanical stirrer and a bottom grain port with 1 kg of *cannabis* distillate and 2 liters of hexane. A 2-liter beaker is charged with 5 grams of sodium perchlorate and 1 liter of water, forming a solution.

The solution is stirred for an adequate length of time (e.g., 5 minutes) until all the salt within the solution dissolves. The water salt solution is then added to the five-liter glass reactor and the mixture is stirred (e.g., manually or via a mechanical and/or electrical stirring mechanism). The stirring continues for a set length of time (e.g., 15 minutes) and then ceases at the conclusion of the set length of time.

After the stirring is concluded, multiple layers of liquid form. Once two liquid layers are formed, a bottom water layer is removed. After the water layer is removed, 1 liter of brine solution is added to the five-liter reactor and stirred for a set length of time (e.g., 5 minutes). At the conclusion of the set length of time, the stirring is stopped. Once the stirring is stopped, multiple liquid layers form, including an organic layer which includes a *cannabis* product. Once two water layers are formed, a lower brine layer is removed.

According to various embodiments, the process of forming and removing the brine layer is repeated one or more times (e.g., 3 times, 4 times, etc.). Once the brine layer is removed for the final time, the organic layer with the *cannabis* product is removed under reduced pressure, producing a substantially sulfur free *cannabis* material.

Another illustrative example is herein described:

According to this secondary illustrative example, a five-liter conical glass reactor is presented with a mechanical stirrer and a bottom grain port with 1 kg of crude *cannabis* material and 2 liters of hexane. The crude *cannabis* material includes extracted *cannabis* material that has not been degummed or dewaxed. A 2-liter beaker is charged with 5 grams of sodium perchlorate and 1 liter of water, forming a solution.

The solution is stirred for an adequate length of time (e.g., 5 minutes) until all the salt within the solution dissolves. The water salt solution is then added to the five-liter glass reactor and the mixture is stirred (e.g., manually or via a mechanical and/or electrical stirring mechanism). The stirring continues for a set length of time (e.g., 15 minutes) and then ceases at the conclusion of the set length of time.

After the stirring is concluded, multiple layers of liquid form. Once two liquid layers are formed, a bottom water layer is removed. After the water layer is removed, 1 liter of brine solution is added to the five-liter reactor and stirred for a set length of time (e.g., 5 minutes). At the conclusion of the set length of time, the stirring is stopped. Once the stirring is stopped, multiple liquid layers form, including an organic layer which includes a *cannabis* product. Once two water layers are formed, a lower brine layer is removed.

According to various embodiments, the process of forming and removing the brine layer is repeated one or more times (e.g., 3 times, 4 times, etc.). Once the brine layer is removed for the final time, the organic layer with the *cannabis* product is removed under reduced pressure, producing a substantially sulfur free *cannabis* material.

B. Compositions, Kits, and Methods of Use

In another aspect of this disclosure, also provided is a composition comprising the *cannabis* product with a reduced sulfur content prepared by the method as described above. The composition further comprises an additive, a pharmaceutical acceptable carrier, or an adjuvant to the *cannabis* component.

The composition can be an oral dosage composition, a pulmonary or nasal dosage composition, or a topical dosage composition. The compositions can be in the form of a solution, a spray, or a powder. In some embodiments, the composition is in the form of a tablet, a capsule, a jelly, a cream, an ointment, a suspension, a spray or a chewing gum.

In certain embodiments, the compositions as described herein are administered via a vaporizer or like device as described, for example, in U.S. Pat. No. 8,915,254; U.S. Pat. Appl. Pub. No. 2014/0060552; U.S. Pat. No. 8,488,952; and U.S. Pat. Appl. Pub. No. 2015/0040926. Compositions for pulmonary administration also include, but are not limited to, dry powder compositions consisting of the powder of a *cannabis* oil described herein, and the powder of a suitable carrier and/or lubricant. The compositions for pulmonary administration can be inhaled from any suitable dry powder inhaler device known to a person skilled in the art. In certain instances, the compositions may be conveniently delivered in the form of an aerosol spray from pressurized packs or a nebulizer, with the use of a suitable propellant, for example, dichlorodifluoro-methane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound(s) and a suitable powder base, for example, lactose or starch.

Pharmaceutical compositions or medicaments can be formulated by standard techniques or methods well-known in the art of pharmacy using one or more physiologically acceptable carriers or excipients. Suitable pharmaceutical carriers are described herein and in, e.g., "Remington's Pharmaceutical Sciences" by E. W. Martin. *Cannabis* oil extracts can be formulated for administration by any suitable route, including, but not limited to, orally, topically, nasally, rectally, vaginally, pulmonary, parenterally (e.g., intravenously, subcutaneously, intramuscularly, etc.), and combinations thereof. In some embodiments, the *cannabis* oil is diluted in a liquid, e.g., a carrier oil. The most suitable route of administration in any given case will depend in part on the condition being treated as well as the response of the subject to the particular route of treatment.

For oral administration, a pharmaceutical composition or a medicament can take the form of, e.g., a tablet or a capsule prepared by conventional means with a pharmaceutically acceptable excipient. Preferred are tablets and gelatin capsules comprising the active ingredient(s), together with (a) diluents or fillers, e.g., lactose, dextrose, sucrose, mannitol, maltodextrin, lecithin, agarose, xanthan gum, guar gum, sorbitol, cellulose (e.g., ethyl cellulose, micro-crystalline cellulose), glycine, pectin, polyacrylates and/or calcium hydrogen phosphate, calcium sulfate, (b) lubricants; e.g., silica, anhydrous colloidal silica, talcum, stearic acid, its magnesium or calcium salt (e.g., magnesium stearate or calcium stearate), metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium or potassium salt, or effervescent mixtures; (e) wetting agents, e.g., sodium lauryl sulfate, and/or (f) absorbents, colorants, flavors, and sweeteners. Tablets can be either uncoated or coated according to methods known in the art. The excipients described herein can also be used for preparation of buccal dosage forms and sublingual dosage forms (e.g., films and lozenges) as described, for example, in U.S. Pat. Nos. 5,981,552 and 8,475,832. Formulation in chewing gums as described, for example, in U.S. Pat. No. 8,722,022, is also contemplated.

Further preparations for oral administration can take the form of, for example, solutions, syrups, suspensions, and toothpastes. Liquid preparations for oral administration can be prepared by conventional means with pharmaceutically acceptable additives, for example, suspending agents, for example, sorbitol syrup, cellulose derivatives, or hydrogenated edible fats; emulsifying agents, for example, lecithin, xanthan gum, or acacia; non-aqueous vehicles, for example, almond oil, sesame oil, hemp seed oil, fish oil, oily esters, ethyl alcohol, or fractionated vegetable oils; and preservatives, for example, methyl or propyl-p-hydroxybenzoate or sorbic acid. The preparations can also contain buffer salts, flavoring, coloring, and/or sweetening agents as appropriate.

Typical formulations for topical administration include creams, ointments, sprays, lotions, hydrocolloid dressings, and patches, as well as eye drops, ear drops, and deodorants. *Cannabis* oils can be administered via transdermal patches as described, for example, in U.S. Pat. Appl. Pub. No. 2015/0126595 and U.S. Pat. No. 8,449,908. Formulation for rectal or vaginal administration is also contemplated. The *cannabis* oils can be formulated, for example, using suppositories containing conventional suppository bases such as cocoa butter and other glycerides as described in U.S. Pat. Nos. 5,508,037 and 4,933,363. Compositions can contain other solidifying agents such as shea butter, beeswax, kokum butter, mango butter, illipe butter, tamanu butter, carnauba wax, emulsifying wax, soy wax, castor wax, rice bran wax, and candelilla wax. Compositions can further include clays (e.g., Bentonite, French green clays, Fuller's earth, Rhassoul clay, white kaolin clay) and salts (e.g., sea salt, Himalayan pink salt, and magnesium salts such as Epsom salt).

The compositions set forth herein can be formulated for parenteral administration by injection, for example, by bolus injection or continuous infusion. Formulations for injection can be presented in unit dosage form, for example, in ampoules or in multi-dose containers, optionally with an added preservative. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure, buffers, and/or other ingredients. Alternatively, the compositions can be in powder form for reconstitution with a suitable vehicle, for example, a carrier oil, before use. In addition, the compositions may also contain other therapeutic agents or substances.

The compositions can be prepared according to conventional mixing, granulating, and/or coating methods, and contain from about 0.1 to about 75%, preferably from about 1 to about 50%, of the *cannabis* oil extract. In general, subjects receiving a *cannabis* oil composition orally are administered doses ranging from about 1 to about 2000 mg of *cannabis* oil. A small dose ranging from about 1 to about 20 mg can typically be administered orally when treatment is initiated, and the dose can be increased (e.g., doubled) over a period of days or weeks until the maximum dose is reached.

In some embodiments, the composition is an oral dosage composition, a pulmonary or nasal dosage composition, or a topical dosage composition. The composition may be in the form of a solution, a spray, or a powder, a tablet, a capsule, a jelly, a cream, an ointment, a suspension, a spray or a chewing gum.

Also within the scope of this disclosure is a unit dose of the composition as described above. In some embodiments, the unit dose comprises an amount of the composition selected from the group consisting of: trace amount, 0.01-0.05 mg, 0.05-0.1 mg, 0.1-0.5 mg, 0.25-1 mg, 0.5-15 mg, 0.5-2.5 mg, 1.0-2.5 mg, 2.5-5 mg, 5.0-7.5 mg, 5.0-10 mg, 1.0-25 mg, 25-50 mg, 50-75 mg, 75-100 mg, 10-20 mg, 10-15 mg, and 15-20 mg, 20-30 mg, 30-40 mg, 40-50 mg, 50-60 mg, 60-70 mg, 70-80 mg, 80-90 mg, 90-100 mg, 1-100 mg, 100-125 mg, 125-150 mg, 150-175 mg, 175-200 mg, and >200 mg.

In some embodiments, the composition may further comprise a second agent selected from the group consisting of: cannabinoids, terpenes, anti-insomnia, anti-tussive opioid analgesic, decongestant, non-opioid analgesic/anti-inflammatory drug, anti-migraine drug, anti-emetic, anti-histamine, proton pump inhibitor, H2 antagonist/H2 blocker, tranquilizer, anticonvulsant, hypnotic, muscle relaxant, antipsychotic, anti-diarrheal, Attention Deficit and Hyperactivity Disorder (ADHD) drug, anti-Parkinson disease drug, benzodiazepine, benzodiazepine antagonist, barbiturate, barbiturate antagonist, stimulant, stimulant antagonist, antidepressant, nutraceutical, nicotine, BCS Class II active ingredient, BCS Class IV active ingredient, an anti-multiple sclerosis (MS) drug, ethyl pyruvate, melatonin, caffeine, resveratrol, and a combination thereof.

In some embodiments, the second agent is selected from the group consisting of: CBD, THC, CBN, CBG, CBC, THCA, CBDA, THCV, and a combination thereof.

In some embodiments, the composition at therapeutically effective concentrations or dosages can be combined with a pharmaceutically or pharmacologically acceptable carrier, excipient or diluent, either biodegradable or non-biodegradable.

For example, the composition may be administered in the pure form or in a pharmaceutically acceptable formulation including suitable elixirs, binders, and the like (also generally referred to a "carriers") or as pharmaceutically acceptable salts (e.g., alkali metal salts such as sodium, potassium, calcium or lithium salts, ammonium, etc.) or other complexes. It should be understood that the pharmaceutically acceptable formulations include liquid and solid materials conventionally utilized to prepare both injectable dosage forms and solid dosage forms such as tablets and capsules and aerosolized dosage forms. In addition, the compounds may be formulated with aqueous or oil-based vehicles. Water may be used as the carrier for the preparation of compositions (e.g., injectable compositions), which may also include conventional buffers and agents to render the composition isotonic. Other potential additives and other materials (preferably those which are generally regarded as safe [GRAS]) include: colorants; flavorings; surfactants (TWEEN, oleic acid, etc.); solvents, stabilizers, elixirs, and binders or encapsulants (lactose, liposomes, etc.). Solid diluents and excipients include lactose, starch, conventional disintegrating agents, coatings, and the like. Preservatives such as methylparaben or benzalkonium chloride may also be used. Depending on the formulation, it is expected that the active composition will consist of about 1% to about 99% of the composition and the vehicular "carrier" will constitute about 1% to about 99% of the composition. The pharmaceutical compositions of the present invention may include any suitable pharmaceutically acceptable additives or adjuncts to the extent that they do not hinder or interfere with the therapeutic effect of the active compound.

Examples of carriers include, but are by no means limited to, for example, poly(ethylene-vinyl acetate), copolymers of lactic acid and glycolic acid, poly(lactic acid), gelatin, collagen matrices, polysaccharides, poly(D,L lactide), poly (malic acid), poly(caprolactone), celluloses, albumin, starch, casein, dextran, polyesters, ethanol, methacrylate, polyurethane, polyethylene, vinyl polymers, glycols, mixtures thereof and the like. Standard excipients include gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidal silicon dioxide, phosphates, sodium dodecyl sulfate, carboxymethylcellulose calcium, carboxymethylcellulose sodium, methylcellulose, hydroxyethylcellulose, hydroxypropyl cellulose, hydroxypropylmethylcellulose phthalate, noncrystalline cellulose, magnesium aluminum silicate, triethanolamine, polyvinyl alcohol, polyvinylpyrrolidone, sugars, and starches. See, for example, Remington: The Science and Practice of Pharmacy, 1995, Gennaro ed.

In some embodiments, the chemicals can be purified and blended together to produce a formulation similar in form to that for Marinol®. In these formulations, the active ingredient is dissolved in sesame seed oil or similar oil and enclosed in a gel-capsule. In other embodiments, the formulation may be arranged to be used as an injectable or as an aerosol. In these embodiments, as will be apparent to one of skill in the art, the appropriate pharmaceutically-acceptable additives may be added so that the pharmaceutical composition is in the appropriate form.

As will be appreciated by one knowledgeable in the art, the formulation may be used as, for example, an antiemetic, appetite stimulant, or as a treatment for nausea, dementia, Alzheimer's disease, glaucoma, high blood pressure, inflammation or multiple sclerosis. For example, when administered to an individual in need of such treatment, the pharmaceutical composition of Δ8-THC and CBD will accomplish at least one of the following: reduce nausea, promote or stimulate appetite, reduce vomiting and/or promote a general feeling of well-being.

Additional Ingredients:

Cannabinoids are susceptible to oxidation and hydrolysis. Over time it is possible for cannabinoids to be exposed to oxygen, hydrogen ions (acids, water), in addition to any other environmental factors that will cause their degradation.

Organic bases can be used to prevent the degradation of the cannabinoids. These organic bases include, but are not limited to, butyl hydroxyl anisole (BHA), butyl hydroxyl toluene (BHT) and sodium ascorbate; at concentrations between 0.001 to 5%>w/w, for example. Organic bases such as the following can improve the stability of cannabinoids from chemical degradation for up to 2 years: BHA 0.001 to 5% w/w, BHT 0.001 to 5% w/w, and combinations of BHA and BHT can also be used.

Antioxidants can be used to prevent or at least inhibit or mitigate the degradation of cannabinoids from oxidation. Examples of antioxidants include: ethanol, polyethylene glycol 300, polyethylene glycol 400, propylene glycol, propylene carbonate, N-methyl-2-pyrrolidones, dimethylacetamide, dimethyl sulfoxide, hydroxypropyl-P-cyclodextrins, sulfobutylether-β-cyclodextrin, a-cyclodextrin, HSPC phospholipid, DSPG phospholipid, DMPC phospholipid, DMPG phospholipid, ascorbyl palmitate, butylated hydroxyanisole, butylated hydroxyanisole, propyl gallate, a-tocopherol, γ-tocopherol, propyl gallate, lecithin, Vitamin E tocopherol, sesamin, sesamol, sesamolin, alpha-tocopherol, ascorbic acid, ascorbyl palmitate, fumaric acid, malic acid, sodium metabisulfite, and EDTA. Specific antioxidant examples include, but are not limited to: Ascorbic Acid: 0.001 to 5% w/w, Vitamin E Tocopherol: 0.001 to 5% w/w, Tocopherol: 0.001 to 5% w/w, and combinations of ascorbic acid, vitamin E tocopherol, and tocopherol can be used for this invention.

Chelating agents can prevent or at least mitigate the degradation of cannabinoids from metal ions in solution. Chelating agents include, but are not limited to, ethylenediaminetetraacetic acid (EDTA), phosphoric acid, polyphosphates, polysaccharides, citric acid and any combination thereof.

Preservatives can be used to prevent microbial spoilage. These preservatives include: methylparabens, ethylparabens, propylparabens, butylparabens, sorbic acid, acetic acid, propionic acid, sulfites, nitrites, sodium sorbate, potassium sorbate, calcium sorbate, benzoic acid, sodium benzonate, potassium benzonate, calcium benzonate, sodium metabisulfite, propylene glycol, benzaldehyde, butylated hydroxytoluene, butylated hydroxyanisole, formaldehyde donors, essential oils, citric acid, monoglyceride, phenol, mercury components and any combination thereof. Specific examples include, but are not limited to, sodium benzoate and potassium sorbate.

Additionally, the pH can be lowered to prevent or retard microbial growth. Lowering the pH below 4.0 is sufficiently low enough to prevent microbial growth for a minimum of 1 month.

Preservatives and/or stabilizers can be added during formulation. Depending on the nature of the preservative/stabilizer, it may be contained in either the oil phase, interfacial layer, or the aqueous continuous phase. Once dissolved the preservatives and stabilizers are released into solution imparting their properties into the aqueous system. This allows beverage manufacturers the ability to instantly create shelf-stable *cannabis*-infused beverages. Beverages made this way can resist microbial growth and chemical degradation for a minimum of 3 months.

The composition can be used for treatment of a subject afflicted with or suffering from nausea, muscular spasms, multiple sclerosis, uterine cramps, bowel cramps, a movement disorder, pain, migraine headache, vertigo, glaucoma, asthma, inflammation, insomnia, high blood pressure, cancer, anxiety, convulsions, depression or psychosis.

Accordingly, in another aspect, this disclosure provides a method of treatment of a subject. The method comprises administering to a subject afflicted with or suffering from nausea, muscular spasms, multiple sclerosis, uterine cramps, bowel cramps, a movement disorder, pain, migraine headache, vertigo, glaucoma, asthma, inflammation, insomnia, high blood pressure, cancer, anxiety, convulsions, depression or psychosis, an effective amount of the composition as described above.

In some embodiments, the composition is administered intratumorally, intravenously, subcutaneously, intraosseously, orally, transdermally, in sustained release, in controlled release, in delayed release, as a suppository, or sublingually. In some embodiments, the composition is administered once, twice, three, or four times per day, or as needed.

The administration of the composition invention may be intermittent, bolus dose, or at a gradual or continuous, constant or controlled rate to a patient. In addition, the time of day and the number of times per day that the pharmaceutical formulation is administered may vary and are best determined by a skilled practitioner such as a physician. Further, the effective dose can vary depending upon factors such as the mode of delivery, gender, age, and other conditions of the patient, as well as the extent or progression of the disease. The compounds may be provided alone, in a mixture containing two or more of the compounds, or in combination with other medications or treatment modalities. The compounds may also be added to blood ex vivo and then be provided to the patient.

In one aspect, this disclosure provides a kit comprising the composition as described above. In some embodiments, the kit further comprising a beverage, wherein the composition and the beverage are in separate containers. In some embodiments, the kit may further include instructional materials.

"Instructional material," as that term is used herein, includes a publication, a recording, a diagram, or any other medium of expression that can be used to communicate the usefulness of any composition and/or compound of the invention in a kit. The instructional material of the kit may, for example, be affixed to a container that contains any composition of the invention or be shipped together with a container which contains any composition. Alternatively, the instructional material may be shipped separately from the container with the intention that the recipient uses the instructional material and any composition cooperatively. Delivery of the instructional material may be, for example, by physical delivery of the publication or other medium of expression communicating the usefulness of the kit, or may alternatively be achieved by electronic transmission, for example, by means of a computer, such as by electronic mail, or download from a website.

Also within the scope of this disclosure is an edible product comprising the composition as described above. In some embodiments, the edible product is selected from a lozenge, candy, chocolate, brownie, cookie, trail bar, cracker, dissolving strip, pastry, bread, or chewing gum.

C. Definitions

To aid in understanding the detailed description of the compositions and methods according to the disclosure, a few express definitions are provided to facilitate an unambiguous disclosure of the various aspects of the disclosure. Unless otherwise defined, all technical and scientific terms used herein have the same meaning as commonly understood by one of ordinary skill in the art to which this disclosure belongs.

The term "*cannabis*" refers to plants of the genus *cannabis*, including *cannabis* saliva, *Cannabis indica*, and *Cannabis ruderalis*.

The term "*cannabis* oil" refers to a mixture of compounds obtained from the extraction of *cannabis* plants. Such compounds include, but are not limited to, cannabinoids, terpenes, terpenoids, and other compounds found in the *cannabis* plant. The exact composition of *cannabis* oil will depend on the strain of *cannabis* that is used for extraction, the efficiency and process of the extraction itself, and any additives that might be incorporated to alter the palatability or improve administration of the *cannabis* oil.

The term "cannabinoid" refers to a chemical compound that shows direct or indirect activity at a cannabinoid receptor. There are two main cannabinoid receptors, CNR1 (also known as CB1) and CNR2 (also known as CB2). Other receptors that research indicates have cannabinoid activity include the GPR55, GPR18, and TRPV1 receptors. The term "phytocannabinoid" refers to cannabinoids that occur in a plant species or are derived from cannabinoids occurring in a plant species. Examples of cannabinoids include, but are not limited to, tetrahy-drocannabinol (THC), cannabidiol (CBD), cannabinol (CBN), cannabigerol (CBG), *canna*-bichromene (CBC), cannabicyclol (CBL), cannabivarin (CBV), tetrahydrocannabivarin (THCV), cannabidivarin (CBDV), cannabichromevarin (CBCV), cannabigerovarin (CBGV), and cannabigerol monomethyl ether (CBGM).

As used herein, CBD refers to cannabidiol.

As used herein, Δ9-THC refers to Δ9-tetrahydrocannabinol.

As used herein, Δ8-THC refers to Δ8-tetrahydrocannabinol.

The term "acidic cannabinoid" refers to a cannabinoid having one or more carboxylic acid functional groups. Examples of acidic cannabinoids include, but are not limited to, tetra-hydrocannabinolic acid (THCA), cannabidiolic acid (CBDA), and cannabichromenic acid (CBC). Acidic cannabinoids are frequently the predominant cannabinoids found in raw (i.e., unprocessed) *cannabis* plant material.

The term "essential oil" refers to natural plant oil typically obtained by distillation and having a chemical composition and organoleptic properties (e.g., fragrance) characteristic of the plant or other sources from which it is extracted.

As used herein, "anti-emetic" refers to compounds capable of reducing nausea, enhancing appetite and/or reducing vomiting in an individual.

The term "water-soluble," as used herein, refers to that 1 mg of material in 1 ml of water gives a clear solution and is water-miscible.

The term "high affinity," as used herein, refers to that the compounds exhibit a Ki in the range of about 0.03 nM to about 80 nM, and preferably from about 0.03 nM to about 50 nM, for either the CB1 or CB2 receptors, or both.

As used herein, "effective amount" refers to the administration of an amount of a given compound that achieves the desired effect. For example, regarding the combination of CBD and Δ8-THC, an "effective amount" is an amount sufficient for or that is capable of reducing nausea or vomiting and/or enhancing appetite in a patient or individual in need of such treatment. The patient may be a human patient.

As used herein, "purified" does not require absolute purity but is instead intended as a relative definition. For example, purification of starting material or natural material to at least one order of magnitude, preferably two or three orders of magnitude is expressly contemplated as falling within the definition of "purified."

As used herein, the term "isolated" requires that the material be removed from its original environment.

As used herein, the terms "subject" and "patient" are used interchangeably irrespective of whether the subject has or is currently undergoing any form of treatment. As used herein, the terms "subject" and "subjects" may refer to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgus monkey, chimpanzee, etc) and a human). The subject may be a human or a non-human. In this context, a "normal," "control," or "reference" subject, patient or population is/are one(s) that exhibit(s) no detectable disease or disorder, respectively.

"Sample," "test sample," and "patient sample" may be used interchangeably herein. The sample can be a sample of, serum, urine plasma, amniotic fluid, cerebrospinal fluid, cells (e.g., antibody-producing cells) or tissue. Such a sample can be used directly as obtained from a patient or can be pretreated, such as by filtration, distillation, extraction, concentration, centrifugation, inactivation of interfering components, addition of reagents, and the like, to modify the character of the sample in some manner as discussed herein or otherwise as is known in the art. The terms "sample" and "biological sample" as used herein generally refer to a biological material being tested for and/or suspected of containing an analyte of interest such as antibodies. The sample may be any tissue sample from the subject. The sample may comprise protein from the subject.

The terms "determining," "measuring," "assessing," and "assaying" are used interchangeably and include both quantitative and qualitative measurement, and include determining if a characteristic, trait, or feature is present or not. Assessing may be relative or absolute. "Assessing the presence of" a target includes determining the amount of the target present, as well as determining whether it is present or absent.

The term "treating" or "treatment" refers to administration of a compound or agent to a subject who has a disorder or is at risk of developing the disorder with the purpose to cure, alleviate, relieve, remedy, delay the onset of, prevent, or ameliorate the disorder, the symptom of the disorder, the disease state secondary to the disorder, or the predisposition toward the disorder.

The terms "prevent," "preventing," "prevention," "prophylactic treatment" and the like refer to reducing the probability of developing a disorder or condition in a subject (e.g., plant), who does not have, but is at risk of or susceptible to developing a disorder or condition.

The terms "decrease," "reduced," "reduction," "decrease," or "inhibit" are all used herein generally to mean a decrease by a statistically significant amount. However, for avoidance of doubt, "reduced," "reduction" or "decrease" or "inhibit" means a decrease by at least 10% as compared to a reference level, for example, a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The word "substantially" does not exclude "completely," e.g., a composition which is "substantially free" from Y may be completely free from Y. Where necessary, the word "substantially" may be omitted from the definition of the invention.

As used herein, the term "approximately" or "about," as applied to one or more values of interest, refers to a value that is similar to a stated reference value. In some embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Unless indicated otherwise herein, the term "about" is intended to include values, e.g., weight percents, proximate to the recited range that are equivalent in terms of the functionality of the individual ingredient, the composition, or the embodiment.

It is noted here that, as used in this specification and the appended claims, the singular forms "a," "an," and "the" include plural reference unless the context clearly dictates otherwise. The terms "including," "comprising," "containing," or "having" and variations thereof are meant to encompass the items listed thereafter and equivalents thereof as well as additional subject matter unless otherwise noted.

The phrases "in one embodiment," "in various embodiments," "in some embodiments," and the like are used repeatedly. Such phrases do not necessarily refer to the same embodiment, but they may unless the context dictates otherwise.

The terms "and/or" or "/" means any one of the items, any combination of the items, or all of the items with which this term is associated.

As used herein, the term "each," when used in reference to a collection of items, is intended to identify an individual item in the collection but does not necessarily refer to every item in the collection. Exceptions can occur if explicit disclosure or context clearly dictates otherwise.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All methods described herein are performed in any suitable order unless otherwise indicated herein or otherwise clearly contradicted by context. In regard to any of the methods provided, the steps of the method may occur simultaneously or sequentially. When the steps of the method occur sequentially, the steps may occur in any order, unless noted otherwise.

In cases in which a method comprises a combination of steps, each and every combination or subcombination of the steps is encompassed within the scope of the disclosure, unless otherwise noted herein.

The section headings as used herein are for organizational purposes only and are not to be construed as limiting the subject matter described.

Each publication, patent application, patent, and other reference cited herein is incorporated by reference in its entirety to the extent that it is not inconsistent with the present disclosure. Publications disclosed herein are provided solely for their disclosure prior to the filing date of the present invention. Nothing herein is to be construed as an admission that the present invention is not entitled to antedate such publication by virtue of prior invention. Further, the dates of publication provided may be different from the actual publication dates which may need to be independently confirmed.

It is understood that the examples and embodiments described herein are for illustrative purposes only and that various modifications or changes in light thereof will be suggested to persons skilled in the art and are to be included within the spirit and purview of this application and scope of the appended claims.

While certain embodiments of the invention have been described using specific terms, such description is for present illustrative purposes only, and it is to be understood that changes and variations to such embodiments, including but not limited to the substitution of equivalent features or parts, and the reversal of various features thereof, may be practiced by those of ordinary skill in the art without departing from the spirit or scope of the present disclosure.

What is claimed is:

1. A method for removing sulfur from a *cannabis* distillate comprising:
   a) dissolving the *cannabis* distillate in an organic solvent of an alkane or an aromatic, forming a dissolved *cannabis* distillate solution;
   b) mixing sodium perchlorate into the dissolved *cannabis* distillate solution, causing the dissolved *cannabis* distillate solution to form into a water solution and an organic solvent solution of an alkane or aromatic, wherein the water solution includes sulfur, and wherein the organic solution includes the *cannabis* distillate;
   c) removing the water solution from the dissolved *cannabis* distillate solution;
   d) washing the dissolved *cannabis* distillate organic solution with a brine solution; and
   e) removing the brine solution from the dissolved *cannabis* distillate organic solution to yield a *cannabis* distillate without sulfur.

2. The method of claim 1, further comprising removing the organic solvent from the organic solvent solution under a reduced pressure.

* * * * *